(12) United States Patent
Spitler (10) Patent No.: US 9,700,358 B2
(45) Date of Patent: Jul. 11, 2017

(54) GUIDED ROD AND ANCHOR SYSTEM FOR USE IN A MINIMALLY INVASIVE SURGERY SPINAL PROCEDURE OR THE LIKE

(71) Applicant: James Q. Spitler, Boca Raton, FL (US)

(72) Inventor: James Q. Spitler, Boca Raton, FL (US)

(73) Assignee: FloSpine LLC, Boca Raton, FL (US)

( * ) Notice: Subject to any disclaimer, the term of this patent is extended or adjusted under 35 U.S.C. 154(b) by 0 days.

(21) Appl. No.: 14/887,705

(22) Filed: Oct. 20, 2015

(65) Prior Publication Data

US 2016/0106474 A1    Apr. 21, 2016

Related U.S. Application Data (60) Provisional application No. 62/066,025, filed on Oct. 20, 2014.

(51) Int. Cl.
*A61B 17/70* (2006.01)

(52) U.S. Cl.
CPC ............................. *A61B 17/7085* (2013.01)

(58) Field of Classification Search
CPC ............ A61B 17/7004; A61B 17/7011; A61B 17/7032; A61B 17/7037; A61B 17/7083; A61B 17/7086; A61B 17/7089; A61B 17/7085; A61B 17/7091; A61B 17/708; A61B 17/863

USPC ........................ 606/86 A, 246–279, 300–315
See application file for complete search history.

(56) References Cited

U.S. PATENT DOCUMENTS

| | | | |
|---|---|---|---|
| 8,308,728 B2* | 11/2012 | Iott ....................... | A61B 17/701 606/86 A |
| 8,956,361 B2* | 2/2015 | Davenport ......... | A61B 17/7032 606/104 |
| 9,078,702 B1* | 7/2015 | Sims ................... | A61B 17/7077 |
| 9,198,698 B1* | 12/2015 | Doose .................. | A61B 17/708 |
| 2014/0277166 A1* | 9/2014 | Brinkman .......... | A61B 17/7083 606/279 |
| 2014/0277200 A1* | 9/2014 | Parker ................ | A61B 17/7076 606/86 A |

* cited by examiner

*Primary Examiner* — Pedro Philogene
(74) *Attorney, Agent, or Firm* — Clements Bernard Walker PLLC; Christopher L. Bernard; Lawrence A. Baratta, Jr.

(57) ABSTRACT

A bone anchor system utilizing an extended tab tulip having rails which extend from a point above the skin of a patient to a point proximal a bone anchor, and a slide member pivotally coupled to a rod, the slide member having engagement features which align to the rails of the extended tabs such that the coupled rod assembly is easily and efficiently guided to a position more proximate to the bone anchor and the rod is simultaneously pivoted into engagement with an adjacent bone anchor under the skin and musculature of the patient, for example.

20 Claims, 7 Drawing Sheets

GUIDED ROD AND ANCHOR SYSTEM FOR USE IN A MINIMALLY INVASIVE SURGERY SPINAL PROCEDURE OR THE LIKE

CROSS-REFERENCE TO RELATED APPLICATION

The present patent application/patent claims the benefit of priority of U.S. Provisional Patent Application No. 62/066,025, filed on Oct. 20, 2014, and entitled "GUIDED ROD AND ANCHOR SYSTEM FOR USE IN A MINIMALLY INVASIVE SURGERY SPINAL PROCEDURE OR THE LIKE," the contents of which are incorporated in full by reference herein.

FIELD OF THE INVENTION

The present invention relates generally to a guided rod and anchor system for use in a minimally invasive surgery (MIS) spinal procedure or the like. More specifically, the present invention relates to a bone anchor system utilizing an extended tab tulip having rails which extend from a point above the skin of a patient to a point proximal a bone anchor, and a slide member pivotally coupled to a rod, the slide member having engagement features which align to the rails of the extended tabs such that the coupled rod assembly is easily and efficiently guided to a position more proximate to the bone anchor and the rod is simultaneously pivoted into engagement with an adjacent bone anchor under the skin and musculature of the patient, for example.

BACKGROUND OF THE INVENTION

A multitude of bone anchor/rod systems exist for affixing adjacent bone segments, such as adjacent levels of the spine in a spinal fusion procedure, for example. In such procedures, pedicle screws or the like are coupled to the adjacent bone segments. Each pedicle screw has a tulip coupled to its head. In a monoxial configuration, this tulip can rotate with respect to the associated screw head. In a polyaxial configuration, the tulip can rotate and/or pivot with respect to the associated screw head. Once placed, a rod is disposed in adjacent tulips and locked into position using a plurality of set screws or the like, thereby locking the overall construct.

This methodology is well known to those of ordinary skill in the art and may be performed via an open procedure or an MIS procedure. In general, an MIS procedure through a portal is preferred, as incision size is minimized, damage to musculature and nerves is minimized, pain is minimized, and recovery time is shortened. Such an MIS procedure, however, presents some significant challenges. After the pedicle screws or the like are placed, the associated rod must be coupled under the skin and musculature of the patient. It is this rod placement/securement task that is addressed by the present invention.

BRIEF SUMMARY OF THE INVENTION

In various exemplary embodiments, the present invention provides a bone anchor system utilizing an extended tab tulip having rails which extend from a point above the skin of a patient to a point proximal a bone anchor, and a slide member pivotally coupled to a rod, the slide member having engagement features which align to the rails of the extended tabs such that the coupled rod assembly is easily and efficiently guided to a position more proximate to the bone anchor and the rod is simultaneously pivoted into engagement with an adjacent bone anchor under the skin and musculature of the patient, for example.

In one exemplary embodiment, the present invention provides a bone anchor and rod assembly, comprising: a bone screw configured to be selectively disposed in a bone segment; a tulip member coupled to the bone screw; one or more elongate tab extenders selectively coupled to the tulip member; and a rod assembly selectively coupled to the one or more elongate tab extenders; wherein the rod assembly is configured to be selectively translated along a length of the one or more elongate tab extenders. Optionally, the one or more elongate tab extenders comprise a pair of opposed elongate tab extenders disposed concentrically about the tulip member. The one or more elongate tab extenders define a slot along the length of the one or more elongate tab extenders. The rod assembly is selectively coupled to the one or more elongate tab extenders via a slider member. The rod assembly comprises a pivoting rod member coupled to the slider member. The rod member is configured to be selectively pivoted perpendicular to the tulip member as the slider member is selectively translated along the length of the one or more elongate tab extenders. The tulip member is configured to one or more of selectively rotate with respect to the bone screw and selectively pivot with respect to the bone screw. The tulip member and the one or more elongate tab extenders form a hollow channel through which a set screw is selectively disposed. At least a portion of the interior of the tulip member and the one or more elongate tab extenders comprise internal threads for receiving an externally threaded set screw. At least a portion of the interior of the rod assembly also comprises internal threads for receiving the externally threaded set screw.

In another exemplary embodiment, the present invention provides a bone anchor and rod assembly, comprising: a bone screw configured to be selectively disposed in a bone segment; a tulip member coupled to the bone screw; one or more elongate tab extenders selectively coupled to the tulip member; and a rod assembly selectively coupled to the one or more elongate tab extenders; wherein the one or more elongate tab extenders define a slot along a length of the one or more elongate tab extenders; and wherein the rod assembly is configured to be selectively translated along the length of the one or more elongate tab extenders. Optionally, the one or more elongate tab extenders comprise a pair of opposed elongate tab extenders disposed concentrically about the tulip member. The rod assembly is selectively coupled to the one or more elongate tab extenders via a slider member. The rod assembly comprises a pivoting rod member coupled to the slider member. The rod member is configured to be selectively pivoted perpendicular to the tulip member as the slider member is selectively translated along the length of the one or more elongate tab extenders. The tulip member is configured to one or more of selectively rotate with respect to the bone screw and selectively pivot with respect to the bone screw. The tulip member and the one or more elongate tab extenders form a hollow channel through which a set screw is selectively disposed. At least a portion of the interior of the tulip member and the one or more elongate tab extenders comprise internal threads for receiving an externally threaded set screw. At least a portion of the interior of the rod assembly also comprises internal threads for receiving the externally threaded set screw.

In a further exemplary embodiment, the present invention provides a bone anchor and rod method, comprising: selectively disposing a bone screw in a bone segment; coupling a tulip member to the bone screw; selectively coupling one or more elongate tab extenders to the tulip member; and selectively coupling a rod assembly to the one or more elongate tab extenders; wherein the rod assembly is configured to be selectively translated along a length of the one or more elongate tab extenders. Optionally, the one or more elongate tab extenders comprise a pair of opposed elongate tab extenders disposed concentrically about the tulip member. The one or more elongate tab extenders define a slot along the length of the one or more elongate tab extenders. The rod assembly is selectively coupled to the one or more elongate tab extenders via a slider member. The rod assembly comprises a pivoting rod member coupled to the slider member. The rod member is configured to be selectively pivoted perpendicular to the tulip member as the slider member is selectively translated along the length of the one or more elongate tab extenders. The tulip member is configured to one or more of selectively rotate with respect to the bone screw and selectively pivot with respect to the bone screw. The tulip member and the one or more elongate tab extenders form a hollow channel through which a set screw is selectively disposed. At least a portion of the interior of the tulip member and the one or more elongate tab extenders comprise internal threads for receiving an externally threaded set screw. At least a portion of the interior of the rod assembly also comprises internal threads for receiving the externally threaded set screw.

BRIEF DESCRIPTION OF THE DRAWINGS

The present invention is illustrated and described herein with reference to the various drawings, in which like reference numbers are used to denote like assembly components/method steps, as appropriate, and in which.

DETAILED DESCRIPTION OF THE INVENTION

Again, in various exemplary embodiments, the present invention provides a bone anchor system utilizing an extended tab tulip having rails which extend from a point above the skin of a patient to a point proximal a bone anchor, and a slide member pivotally coupled to a rod, the slide member having engagement features which align to the rails of the extended tabs such that the coupled rod assembly is easily and efficiently guided to a position more proximate to the bone anchor and the rod is simultaneously pivoted into engagement with an adjacent bone anchor under the skin and musculature of the patient, for example.

Figure 1:
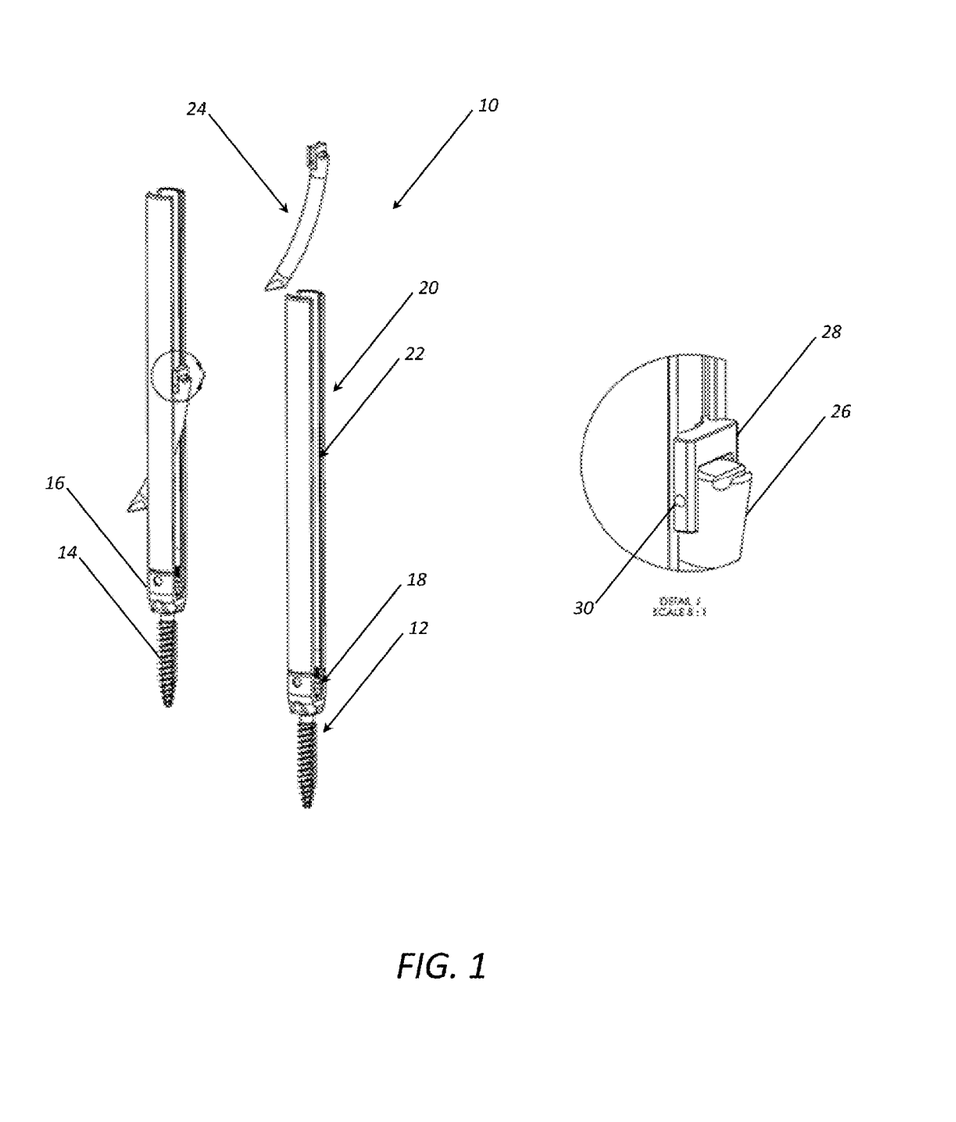
FIG. 1 is a series of perspective views of one exemplary embodiment of the bone anchor and rod assembly of the present invention, highlighting the engagement of the sliding and pivoting rod assembly with the extended tabs of the tulip of the bone anchor.

Referring now specifically to FIG. 1, in one exemplary embodiment, the bone anchor and rod assembly 10 of the present invention includes a bone anchor 12 consisting of a bone screw 14 (such as a pedicle screw or the like) having a head or the like and a tulip 16 coupled to the bone screw 14. In general, this bone anchor 12 resembles a multitude of other conventional bone anchors, in that it is driven into a bone segment and the tulip 16 may be monoxial or polyaxial until it is locked into place, typically by placing a rod and driving a set screw or the like into the recesses and saddle 18 of the tulip 16 and onto the rod. Accordingly, the tulip 16 may be internally threaded and the set screw may be externally threaded. It will be readily apparent to those of ordinary skill in the art that many different types of bone anchors may be used equally with the other concepts and techniques of the present invention.

A pair of concentrically arranged tab extenders 20 extend from the top of the tulip 16 to a point above the skin of the patient when in use. Preferably, these tab extenders 20 are externally threaded at the bottom and engage corresponding internal threads of the tulip 16, or are otherwise removably coupled to the tulip 16. Further, the tab extenders 20 are internally threaded, at least at the bottom, and this internal threading matches that of the tulip 16, such that the set screw may ultimately be driven down through the tab extenders 20 and into the tulip 16, where it ultimately locks the rod in place. The tab extenders 20 define at least one slot 22 that traverses the length of the tab extenders 20, from the top to the tulip 16. This slot 22 acts as a track or rail along which the sliding, pivoting rod assembly 24 is translated, from the top of the tab extenders 20 into the tulip 16. Accordingly, the rod assembly 24 includes a rod member 26 that is pivotably coupled to a slider member 28 via a pin 30 or the like. The engagement of the slider member 28 and the tab extenders 20 is discussed in greater detail herein below, but functionally the slider member 28 is disposed within the slot 22 of the tab extenders 20 and translated along the tab extenders 20 towards and into the tulip 16. At the same time, the rod member 26 is permitted to pivot from a stowed position substantially inside the tulip 16, where the end of the rod member 26 passes into and through (and is ultimately secured to) the tulip 16 of an adjacent bone anchor 12 that has been secured to an adjacent bone segment. In this exemplary embodiment, the slot 22 runs along one side of the tab extenders 20.

Figure 2:
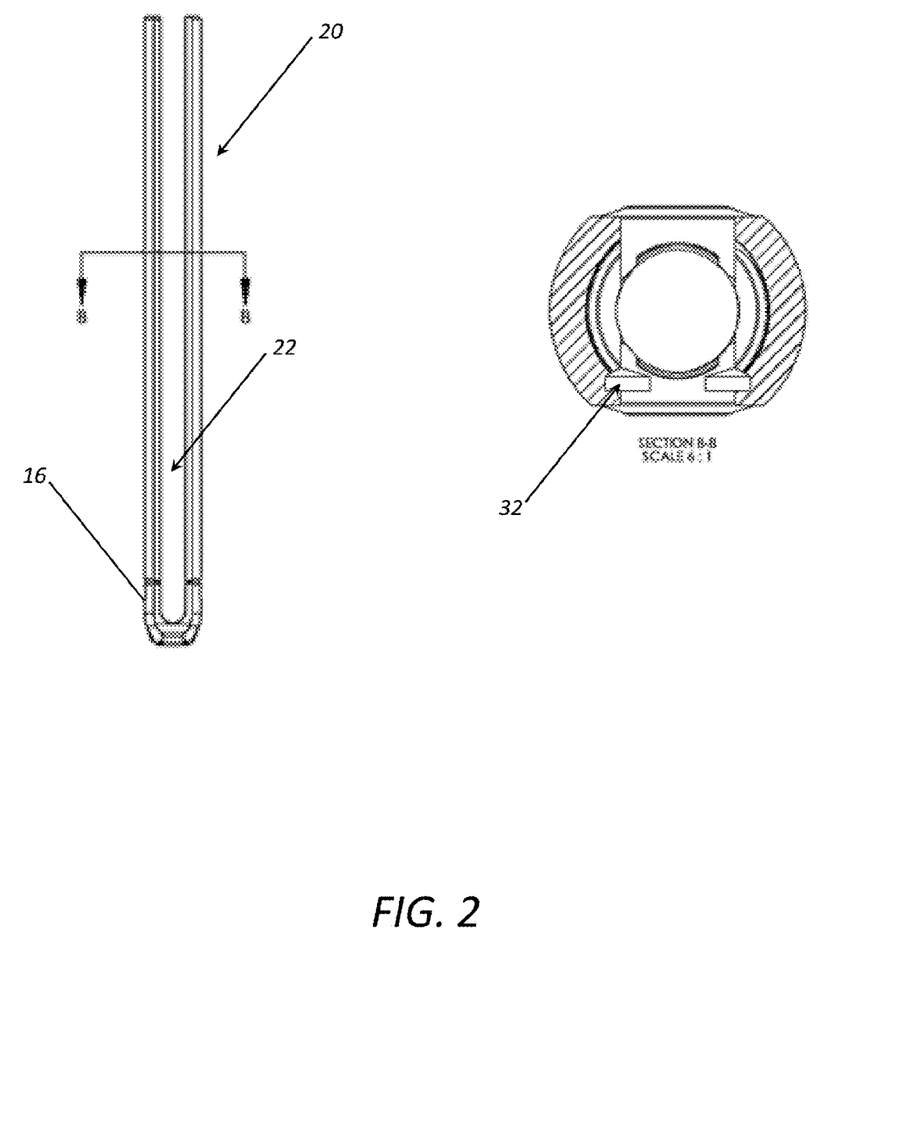
FIG. 2 is a series of planar and cross-sectional views of one exemplary embodiment of the bone anchor of the present invention, highlighting the extended tabs of the tulip of the bone anchor.
Figure 3:
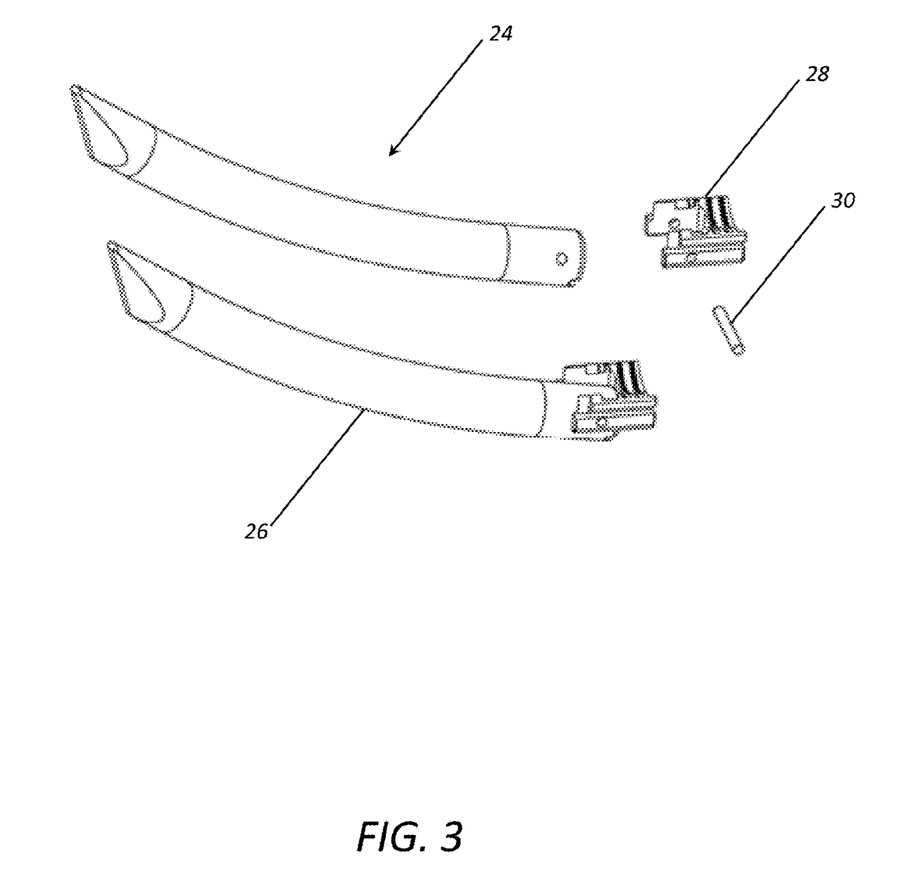
FIG. 3 is a series of perspective views of one exemplary embodiment of the rod assembly of the present invention, highlighting the sliding and pivoting rod assembly.
Figure 4:
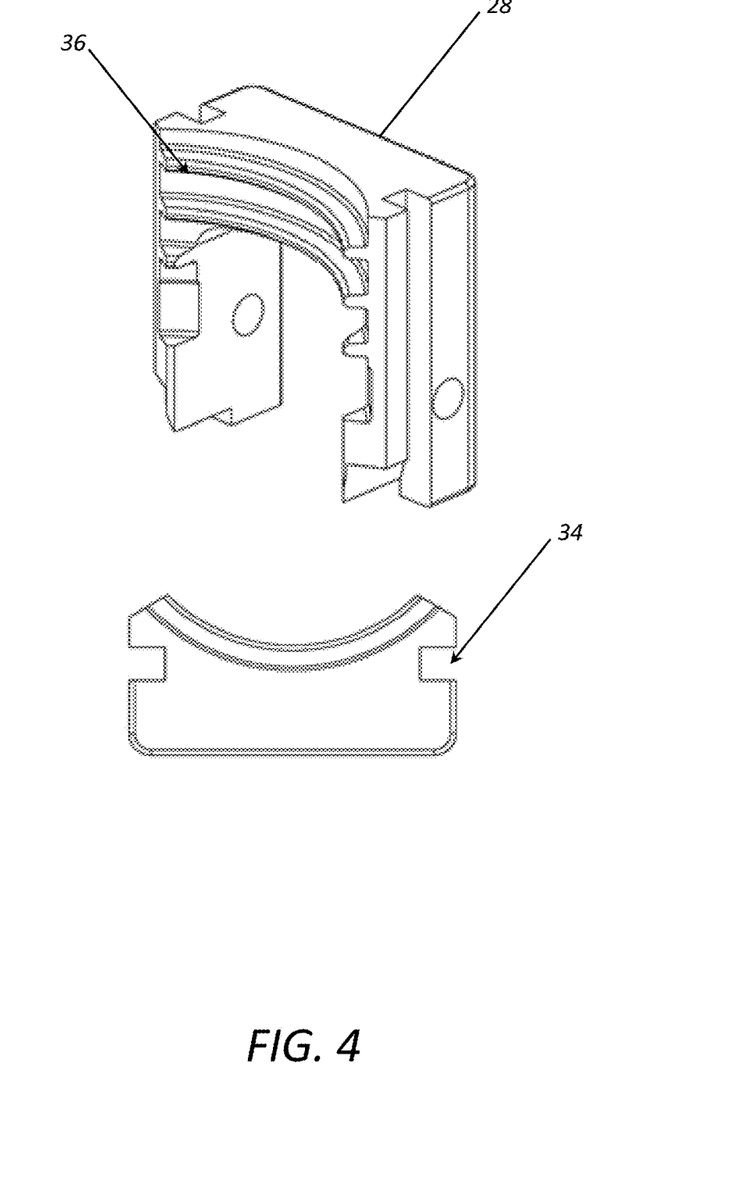
FIG. 4 is a series of perspective and planar views of one exemplary embodiment of the rod assembly of the present invention, highlighting the sliding and pivoting rod assembly.

Referring now specifically to FIGS. 2-4, in one exemplary embodiment, the tab extenders 20 again define at least one slot 22 that traverses the length of the tab extenders 20, from the top to the tulip 16. This slot 22 acts as a track or rail along which the sliding, pivoting rod assembly 24 is translated, from the top of the tab extenders 20 into the tulip 16. Accordingly, the rod assembly 24 includes a rod member 26 that is pivotably coupled to a slider member 28 via a pin 30 or the like. Internally, the tab extenders 20 define a pair of opposed translation channels/rails 32 that are engaged by a pair of opposed translation channels/rails 34 of the slider member 28. Collectively, these features allow the sliding, pivoting rod assembly 24 to be translated, from the top of the tab extenders 20 into the tulip 16. In this exemplary embodiment, the slider member 28 also defines a partial internal thread 36 that is ultimately configured to receive the set screw or the like when the slider member 28 is fully deployed and the rod member 26 is fully seated in the tulip 16. In this respect, the slider member 28 fills a recess manufactured into the side of the tulip 16 and forms a portion of the wall thereof. The partial internal thread 36 of the slider member 28 lines up with the internal thread of the tulip 16, and these internal threads collectively receive the set screw or the like when the slider member 28 is fully deployed and the rod member 26 is fully seated in the tulip 16, thereby securing the slider member 28 and the rod member 26 in the tulip 16 below the tab extenders 20.

Figure 5:
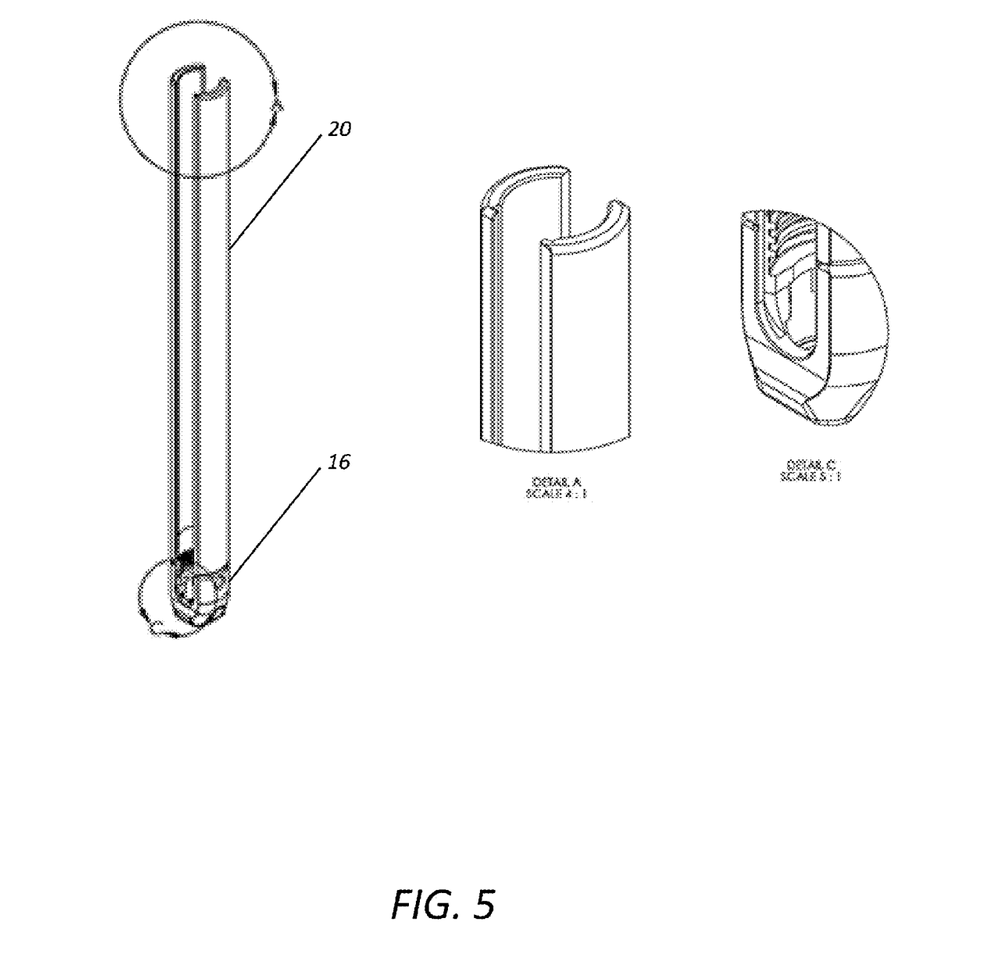
FIG. 5 is a series of perspective views of one exemplary embodiment of the bone anchor of the present invention, again highlighting the extended tabs of the tulip of the bone anchor and the associated internal threading.

Referring to specifically to FIG. 5, in one exemplary embodiment, as alluded to herein above, the tulip 16 is internally threaded and the set screw may be externally threaded. Preferably, the tab extenders 20 are externally threaded at the bottom and engage corresponding internal threads of the tulip 16, or are otherwise removably coupled to the tulip 16. Further, the tab extenders 20 are internally threaded, at least at the bottom, and this internal threading matches that of the tulip 16, such that the set screw may ultimately be driven down through the tab extenders 20 and into the tulip 16, where it ultimately locks the rod in place in conjunction with the partial internal thread 36 of the slider member (FIG. 4), as also alluded to herein above.

Figure 6:
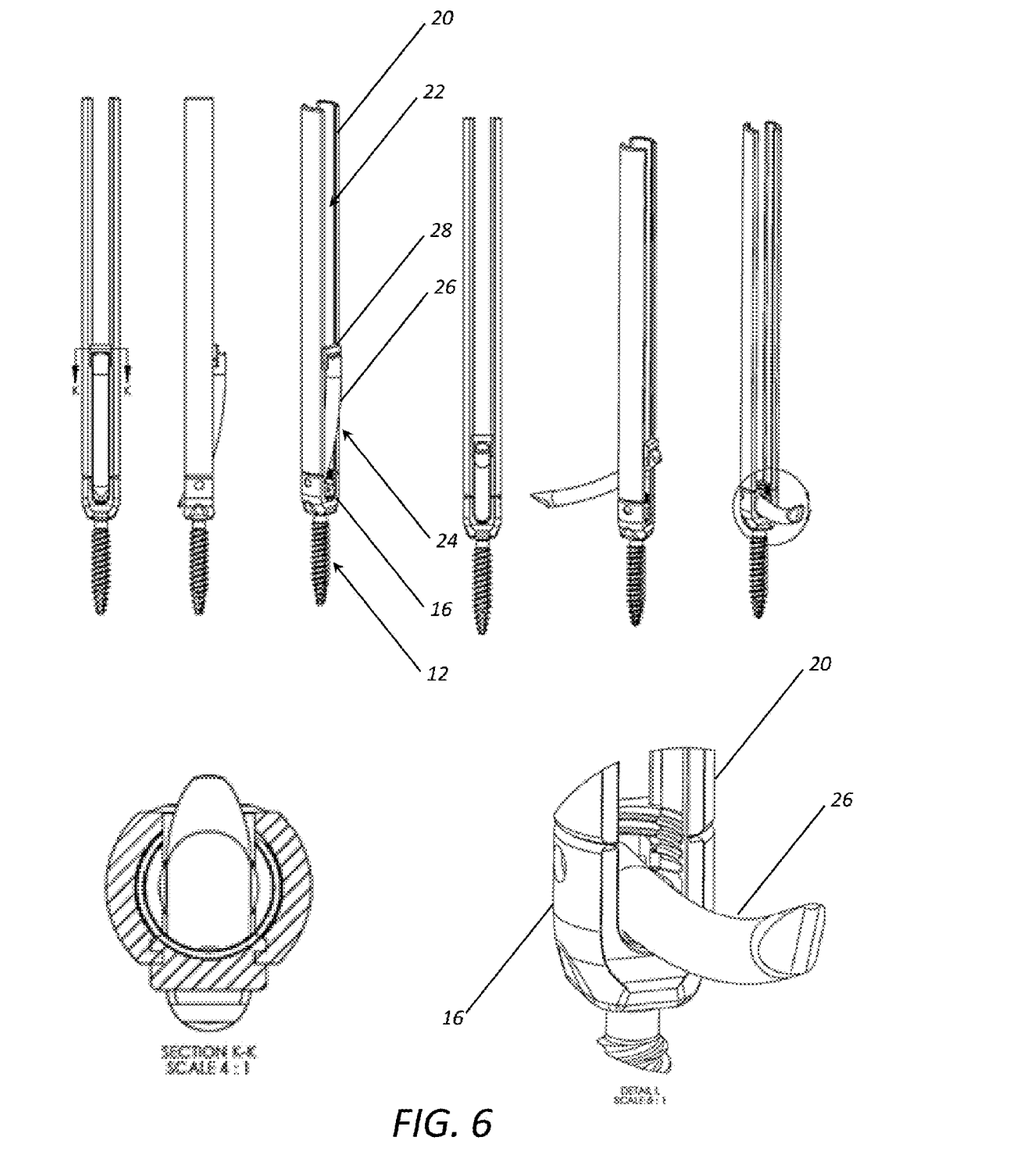
FIG. 6 is a series of perspective and cross-sectional views of one exemplary embodiment of the bone anchor and rod assembly of the present invention, highlighting the engagement of the sliding and pivoting rod assembly with the extended tabs of the tulip of the bone anchor.

Referring now specifically to FIG. 6, in one exemplary embodiment, functionally the slider member 28 is disposed within the slot 22 of the tab extenders 20 and translated along the tab extenders 20 towards and into the tulip 16. At the same time, the rod member 26 is permitted to pivot from a stowed position substantially inside the tulip 16, where the end of the rod member 26 passes into and through (and is ultimately secured to) the tulip 16 of an adjacent bone anchor that has been secured to an adjacent bone segment. Thus, the rod assembly 24 is easily and efficiently guided to a position more proximate to the bone anchor 12 and the rod member 26 is simultaneously pivoted into engagement with the adjacent bone anchor under the skin and musculature of the patient, for example. Subsequent to such placement, the tab extenders 20 may be removed and the incision site closed, as in conventional surgical procedures.

Figure 7:
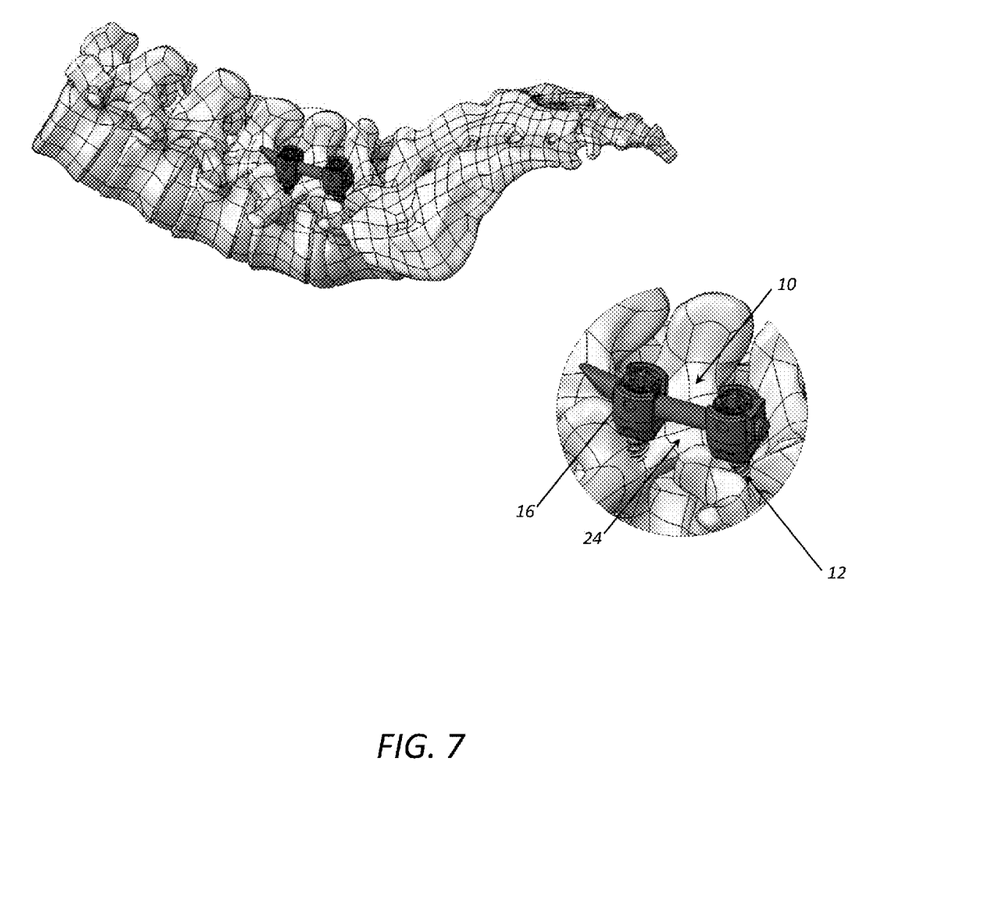
FIG. 7 is a series of perspective views of one exemplary embodiment of the bone anchor and rod assembly of the present invention, highlighting the engagement of the pivoting rod assembly with the tulips of adjacent bone anchors in an installed configuration.

FIG. 7 is a series of perspective views of one exemplary embodiment of the bone anchor and rod assembly 10 of the present invention, highlighting the engagement of the pivoting rod assembly 24 with the tulips 16 of adjacent bone anchors 12 in an installed configuration.

It will be readily apparent to those of ordinary skill in the art that all of the components of the present invention may be manufactured from conventional metallic, ceramic, or polymeric materials that are suitable for surgical applications using conventional manufacturing techniques. In this sense, the bone anchor 12 of the present invention resembles a multitude of other conventional bone anchors.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following non-limiting claims.

What is claimed is:

1. A bone anchor and rod assembly, comprising:
   a bone screw configured to be selectively disposed in a bone segment;
   a tulip member coupled to the bone screw;
   one or more elongate tab extenders selectively coupled to the tulip member, wherein the one or more elongate tab extenders define a slot along the length of the one or more elongate tab extenders; and
   a rod assembly selectively coupled to the one or more elongate tab extenders, wherein the rod assembly is selectively coupled to the one or more elongate tab extenders via a slider member that translates within the slot defined along the length of the one or more elongate tab extenders, and wherein the rod assembly comprises a pivoting rod member pivotably coupled to the slider member;
   wherein the rod assembly is configured to be selectively translated along a length of the one or more elongate tab extenders.

2. The bone anchor and rod assembly of claim 1, wherein the one or more elongate tab extenders comprise a pair of opposed elongate tab extenders disposed concentrically about the tulip member.

3. The bone anchor and rod assembly of claim 1, wherein the rod member is configured to be selectively pivoted perpendicular to the slider member and the tulip member as the slider member is selectively translated along the length of the one or more elongate tab extenders.

4. The bone anchor and rod assembly of claim 1, wherein the tulip member is configured to one or more of selectively rotate with respect to the bone screw and selectively pivot with respect to the bone screw.

5. The bone anchor and rod assembly of claim 1, wherein the tulip member and the one or more elongate tab extenders form a hollow channel through which a set screw is selectively disposed.

6. The bone anchor and rod assembly of claim 5, wherein at least a portion of the interior of the tulip member and the one or more elongate tab extenders comprise internal threads for receiving an externally threaded set screw.

7. The bone anchor and rod assembly of claim 6, wherein at least a portion of the interior of the rod assembly also comprises internal threads for receiving the externally threaded set screw.

8. A bone anchor and rod assembly, comprising:
   a bone screw configured to be selectively disposed in a bone segment;
   a tulip member coupled to the bone screw;
   one or more elongate tab extenders selectively coupled to the tulip member, wherein the one or more elongate tab extenders define a slot along the length of the one or more elongate tab extenders; and
   a rod assembly selectively coupled to the one or more elongate tab extenders, wherein the rod assembly is selectively coupled to the one or more elongate tab extenders via a slider member that translates within the slot defined along the length of the one or more elongate tab extenders, and wherein the rod assembly comprises a pivoting rod member pivotably coupled to the slider member;
   wherein the rod assembly is configured to be selectively translated along the length of the one or more elongate tab extenders; and
   wherein the rod member is configured to be selectively pivoted perpendicular to the slider member and the tulip member as the slider member is selectively translated along the length of the one or more elongate tab extenders.

9. The bone anchor and rod assembly of claim 8, wherein the one or more elongate tab extenders comprise a pair of opposed elongate tab extenders disposed concentrically about the tulip member.

10. The bone anchor and rod assembly of claim 8, wherein the tulip member is configured to one or more of selectively rotate with respect to the bone screw and selectively pivot with respect to the bone screw.

11. The bone anchor and rod assembly of claim 8, wherein the tulip member and the one or more elongate tab extenders form a hollow channel through which a set screw is selectively disposed.

12. The bone anchor and rod assembly of claim 11, wherein at least a portion of the interior of the tulip member and the one or more elongate tab extenders comprise internal threads for receiving an externally threaded set screw.

13. The bone anchor and rod assembly of claim 12, wherein at least a portion of the interior of the rod assembly also comprises internal threads for receiving the externally threaded set screw.

14. A bone anchor and rod method, comprising:
selectively disposing a bone screw in a bone segment;
coupling a tulip member to the bone screw;
selectively coupling one or more elongate tab extenders to the tulip member, wherein the one or more elongate tab extenders define a slot along the length of the one or more elongate tab extenders; and
selectively coupling a rod assembly to the one or more elongate tab extenders, wherein the rod assembly is selectively coupled to the one or more elongate tab extenders via a slider member that translates within the slot defined along the length of the one or more elongate tab extenders, and wherein the rod assembly comprises a pivoting rod member pivotably coupled to the slider member;
wherein the rod assembly is configured to be selectively translated along a length of the one or more elongate tab extenders.

15. The bone anchor and rod assembly of method of claim 14, wherein the one or more elongate tab extenders comprise a pair of opposed elongate tab extenders disposed concentrically about the tulip member.

16. The bone anchor and rod method of claim 14, wherein the rod member is configured to be selectively pivoted perpendicular to the slider member and the tulip member as the slider member is selectively translated along the length of the one or more elongate tab extenders.

17. The bone anchor and rod method of claim 14, wherein the tulip member is configured to one or more of selectively rotate with respect to the bone screw and selectively pivot with respect to the bone screw.

18. The bone anchor and rod method of claim 14, wherein the tulip member and the one or more elongate tab extenders form a hollow channel through which a set screw is selectively disposed.

19. The bone anchor and rod method of claim 18, wherein at least a portion of the interior of the tulip member and the one or more elongate tab extenders comprise internal threads for receiving an externally threaded set screw.

20. The bone anchor and rod method of claim 19, wherein at least a portion of the interior of the rod assembly also comprises internal threads for receiving the externally threaded set screw.

* * * * *